(12) United States Patent
Kawaji et al.

(10) Patent No.: US 6,262,121 B1
(45) Date of Patent: Jul. 17, 2001

(54) OILY PATCHES FOR EXTERNAL USE CONTAINING DICLOFENAC SODIUM

(75) Inventors: Toshikuni Kawaji; Masahiro Yamaji, both of Kagawa-ken (JP)

(73) Assignee: Teikoku Seiyaku Co., Ltd., Kagawa-ken (JP)

(*) Notice: Subject to any disclaimer, the term of this patent is extended or adjusted under 35 U.S.C. 154(b) by 0 days.

(21) Appl. No.: 09/254,925

(22) PCT Filed: Jul. 14, 1998

(86) PCT No.: PCT/JP98/03135

§ 371 Date: May 17, 1999

§ 102(e) Date: May 17, 1999

(87) PCT Pub. No.: WO99/03461

PCT Pub. Date: Jan. 28, 1999

(30) Foreign Application Priority Data

Jul. 18, 1997 (JP) .................................................. 9-193759

(51) Int. Cl.[7] .......................... A31K 31/195; A61K 9/70
(52) U.S. Cl. ............................................. 514/567; 424/449
(58) Field of Search ........................... 423/443; 514/567, 514/934, 944, 945; 424/447, 448, 449

(56) References Cited

U.S. PATENT DOCUMENTS

| | | | |
|---|---|---|---|
| 4,455,146 | * | 6/1984 | Noda et al. ........................... 424/448 |
| 5,472,982 | | 12/1995 | Suzuki . |
| 5,725,874 | * | 3/1998 | Oda et al. ............................. 424/443 |

FOREIGN PATENT DOCUMENTS

| | | | |
|---|---|---|---|
| 0428352A1 | 5/1991 | (EP) . | |
| 879597 | * 11/1998 | (EP) | ............................. A61K/31/195 |
| 54-138124 | 10/1979 | (JP) . | |
| 55-133310 | 10/1980 | (JP) . | |
| 59-33211 | 2/1984 | (JP) . | |
| 59-76013 | 4/1984 | (JP) . | |
| 61-60608 | 3/1986 | (JP) . | |
| 63-150221A | 6/1988 | (JP) . | |
| 6413020 | 1/1989 | (JP) . | |
| 1297059 | 11/1989 | (JP) . | |
| 1297069 | 11/1989 | (JP) . | |
| 4321624 | 11/1992 | (JP) . | |
| 5148145 | 6/1993 | (JP) . | |
| 648939 | 2/1994 | (JP) . | |
| 656660 | 3/1994 | (JP) . | |
| 6219940 | 8/1994 | (JP) . | |
| 6321771 | 11/1994 | (JP) . | |
| 789853 | 4/1995 | (JP) . | |
| 7165564 | 6/1995 | (JP) . | |
| 8119859 | 5/1996 | (JP) . | |
| 8165240 | 6/1996 | (JP) . | |
| 8319234 | 12/1996 | (JP) . | |
| 9208463 | 8/1997 | (JP) . | |
| 10147521 | 6/1998 | (JP) . | |

* cited by examiner

*Primary Examiner*—William R. A. Jarvis
*Assistant Examiner*—Vickie Kim
(74) *Attorney, Agent, or Firm*—Birch, Stewart, Kolasch & Birch, LLP

(57) ABSTRACT

The oil patches containing diclofenac sodium which are characterized in that diclofenac sodium, isostearic acid and a fatty acid having 10 to 18 carbon atoms which is liquid at ordinary temperature are combined in an adhesive.

12 Claims, No Drawings

OILY PATCHES FOR EXTERNAL USE CONTAINING DICLOFENAC SODIUM

This application is the national phase under 35 U.S.C. §371 of prior PCT International Application No. PCT/JP98/03135 which has an International filing date of Jul. 14, 1998 which designated the United States of America.

TECHNICAL FIELD

The present invention relates to external oil patches containing diclofenac sodium which hardly show skin irritation and which do not decrease of release of the said drug.

BACKGROUND ART

Diclofenac sodium is sold as non-steroidal anti-inflamatoric antipyretic analgesics in the form of tablets, capsules or suppositories for the purpose of systemic action. When diclofenac sodium is orally administered, side effects on the stomach, such as stomach unpleasant feelings, occur. To reduce such side effects, therefore, preparations for transdermal absorption of diclofenac sodium have been studied.

Because diclofenac sodium hardly dissolves in water and an oil base, external preparations containing diclofenac sodium are prepared in the state of dispersion of diclofenac sodium. However, transdermal absorption of diclofenac sodium is not good in the state of dispersion preparations. Accordingly, techniques to dissolve diclofenac sodium in external preparations by additives have been developed.

There are, for instance, known external preparations, such as oil ointments characterized in using propylene glycol etc. as a solubilizing agent in order to solve the problem on insolubility of diclofenac sodium in an oil base (Japanese Patent Publication No. 59-33211), gel preparations characterized in using a definite amount of an alcohol, considering that diclofenac sodium dissolves well in an alcohol (Japanese Patent Publication No. 59-76013), emulsion preparations characterized in using a fatty acid and a carboxylic acid dialkyl ester (Japanese Patent Publication No. 64-13020).

Furthermore, following preparations are proposed: poultices characterized in using ethanol/water as a solvent, poultices characterized in using an alkylene glycol having 3 to 4 carbon atoms as a solvent with maintaining moisture (Japanese Patent Publication No. 61-60608), patches containing styrene-isoprene-styrene block copolymer and crotamiton (Japanese Patent Publication No. 4-321624), preparations for transdermal administration characterized in using a base consisting of a fatty acid ester, an alcohol and water (Japanese Patent Publication No. 6-321771), transdermal preparations containing urea or sodium edetate (Japanese Patent Publication No. 6-48939) and so on.

DISCLOSURE OF INVENTION

In the above oil ointments, solubility of diclofenac sodium is improved, but its transdermal absorption is not necessarily satisfied.

In case of the above gel preparations, it is difficult to control the amount of administration of diclofenac sodium and it is necessary to wrap with a bandage and the like, due to being afraid of adhesion on clothes and it is troublesome. Furthermore, in case of preparations in which an alcohol is used, diclofenac sodium is crystallized owing to volatility of the alcohol and by contacting skin with the alcohol for a long term, there is a possibility to cause skin irritation.

In the above emulsion preparations, it is difficult to control the amount of administration of diclofenac sodium and there is afraid of adhesion on clothes as in the gel preparations. Further, regarding a surfactant for emulsification, depending on its amount in the preparations or its kind, there is a possibility of occurrence of skin irritation.

In case of the above poultices, owing to using ethanol there is afraid of generation of crystals of diclofenac sodium and skin irritation as in the above gel preparations. In case of using an alkylene glycol, transdermal absorption of diclofenac sodium is not necessarily satisfied. In case of the above patches containing styrene-isoprene-styrene block copolymer and crotamiton, solubility of diclorofenac sodium is improved, but they are not necessarily satisfied.

In case of the above preparations for transdermal administration containing a fatty acid ester, an alcohol and water, there is a possibility of occurrence of skin irritation owing to using the alcohol.

The above preparations containing urea or sodium edetate are creams and therefore, it is difficult to control the amount of the drug.

Furthermore, in order to improve transdermal absorption of diclofenac sodium, it is tried to combine a fatty acid, such as oleic acid, linoleic acid, linolenic acid, etc. in diclofenac sodium and make the fatty acid capture sodium ion to produce the free acid and as a result to improve transdermal absorption of diclofenac sodium. However, because in this case, sodium salt of the fatty acid is produced at the same time, there is a possibility to cause skin irritation by its salt.

As mentioned above, regarding to known external preparations containing diclofenac sodium, there is a problem on its transdermal absorption and even if the problem is solved, there is still another problem on skin irritation.

Therefore, it has been desired to develop external preparations without skin irritation in which diclofenac sodium is effectively percutaneously absorbed.

The present inventors engaged in extensively in solving above problems, and found to make external oil patches containing diclofenac sodium which show hardly irritation to skin without decrease of release of the said drug by combining a fatty acid having 10 to 18 carbon atoms which is liquid at ordinary temperature and isostearic acid in an adhesive.

More specifically, diclofenac sodium is dissolved in a mixture (oil base) of isostearic acid, a fatty acid having 10 to 18 carbon atoms which is liquid at ordinary temperature and a liquid oil, such as crotamiton, diethyl sebacate, isopropyl myristate, etc., and the resulting solution (drug solution) is admixed in a solution of styrene-isoprene-styrene block copolymer (abbreviated as SIS) and a tackifier resin, and then the mixture is spread on the silicon treated liner and after drying, is stuck on the soft backing to prepare transdermal patches, which patches have excellent adhesiveness and drug release and show hardly skin irritation. Thus, the present invention was completed.

The present invention was explained more in detail as follows.

The amount of diclofenac sodium which is a main ingredient of the patches related to the present invention (it may be abbreviated as the drug) is 0.5 to 6% by weight per total adhesive base material, preferably 2 to 5%, and more preferably 2.5 to 4.5%. In case of less than 0.5%, owing to the less of the drug release, the effect of the drug is not expected. On the other hand, in case of beyond 6%, it becomes hardly to dissolve the drug in the preparation. Either case is not preferable.

The amount of the oil base is 8 to 30% by weight per total adhesive base material, preferably 10 to 25% and more preferably 17 to 22%. In case of less than 8%, release of the drug from the preparation is not enough and the effect of the drug is not expected. On the other hand, in case of beyond 30%, adhesive power especially decreases and therefore, it is impossible to adhere to the skin for long hours.

The ratio of a fatty acid and a liquid oil, such as crotamiton, isopropyl myristate, etc. which are used as an oil base is preferably 1:2 to 2:1.

Examples of fatty acids having 10 to 18 carbon atoms which are liquid at ordinary temperature used in the patches of the present invention are capric acid, 2-undecylenic acid, 10-undecylenic acid, undecylic acid, trans-2-dodecenic acid, 2-hexyl decanoic acid, licinolic acid, linolenic acid, oleic acid, cis-6-octadecenoic acid, linoleic acid, petroselinic acid, etc., preferably capric acid, oleic acid, linoleic acid, linolenic acid and more preferably oleic acid and linolenic acid.

The ratio of isostearic acid and a fatty acid having 10 to 18 carbon atoms which is liquid at ordinary temperature is 8:2 to 4:6, preferably 15:5 to 9:11, and more preferably 7:3 to 5:5. In case of beyond 80% in the amount of isostearic acid, it is impossible to dissolve the drug and release of the drug from the preparation become less. Therefore, it is not preferable. On the other hand, in case of beyond 60% in the amount of a liquid fatty acid, skin irritation on application occurs and therefore, it is not also preferable.

The amount of the mixture of isostearic acid and a fatty acid having 10 to 18 carbon atoms which is liquid at ordinary temperature is preferably 2 to 15% by weight per adhesive base material, more preferably 3 to 10%. In case of less than 2%, the drug from the preparation does not release enough and in case of beyond 15%, adhesive power of the preparation decreases. Either is not preferable.

When a fatty acid having less than 10 carbon atoms is used, skin permeability of the drug extremely decreases and further adhesive power of the preparation decreases. Therefore, it is impossible to adhere such a preparation for long hours. Accordingly, to use such fatty acids should be avoided. On the other hand, when a fatty acid having beyond 18 carbon atoms is used, among them a fatty acid which is solid at ordinary temperature can hardly dissolve dicrofenac sodium and decrease of skin permeability is resulted. The fatty acid which is liquid at ordinary temperature is readily oxidized and deterioration of it occurs because there are many unsaturated bonds in the carbon chain. Therefore, such fatty acids are not preferable.

The tackifier resins used as an adhesive agent of the present invention include a rosin, terpene resin, petroleum resin, phenolic resin, xylene resin, etc.

The amount of the tackifier resin is 25 to 50% by weight, preferably 30 to 45%, and more preferably 35 to 40%. In case of less than 25%, adhesive power decreases and it is not preferable. And in case of beyond 50%, the adhesive base material becomes hard and cohesive power is reduced. It is also not preferable.

The amount of SIS is preferably 30 to 50% by weight, more preferably 35 to 45%. In case of less than 30%, residual and reduction of cohesive power occur, and in case of beyond 50%, adhesive power of the preparation is reduced. Either case is not preferable.

It is preferable to add an antioxidant for stabilization in preparing the preparations or for preservation. Examples of the antioxidants are pentaerythrityl·tetrakis[3-(3,5-di-t-butyl-4-hydroxyphenyl)]propionate, butyl hydroxyanisole, tocopherol, dibutyihydroxytoluene, etc. The amount of the antioxidant is 0.1 to 2% by weight per total adhesive base material. The amount less than 0.1% is not preferable because sufficient effect of the antioxidant is not expected. In case of beyond 2%, crystals of diclofenac sodium are produced and reduction of skin permeability results and it is not preferable.

If desired, a fat and oil, such as liquid paraffin, vaseline, etc., a softener such as a liquid gum (e.g. polybutene, polyisobutylene, polyisoprene and so on) and a perfume, such as l-menthol, dl-camphor, etc. may be admixed in the patches of the present invention.

The patches of the present invention are prepared, for example, by the following methods.

Diclorofenac sodium is dissolved under warming at about 70° C. in a mixture (oil base) of a liquid oil, such as crotamiton, isopropyl myristate, etc., isostearic acid and a fatty acid having 10 to 18 carbon atoms which is liquid at ordinary temperature, such as oleic acid etc. to prepare a drug solution. On the other hand by using toluene etc., a 40% SIS solution is prepared. A saturated alicyclic hydrocarbon petroleum resin (tackifier resin: abbreviated as Petroleum resin) and an antioxidant are added to the SIS solution and dissolved. The prepared adhesive solution and the drug solution are mixed under stirring. The resulting mixture is spread on the liner by a conventional method and after elimination of the solvent by drying, laminated with a backing and cut in desired size to prepare the preparation. The amount of the spread adhesive after drying is 30 to 200 g/m$^2$, preferably 50 to 100 g/m$^2$.

Further, the preparations of the present invention can be also prepared by hot-melt method as follows: a SIS (adhesive agent), a tackifier resin and an antioxidant are dissolved under heating (about 120–160° C.) and the drug solution is admixed and the resulting mixture is spread on the liner and laminated with a backing to prepare the preparation.

The backing is preferable in being rich in flexibility in order to fix for long hours, typically such as woven textile or felt made from polyester fiber.

BEST MODE FOR CARRYING OUT THE INVENTION

The present invention is shown in more detail by the following Examples and Comparative Examples. But the present invention is not limited by Examples and in view of the before or after the descriptions, if desired, to make modification should be recognized to be included in the scope of the present invention.

According to the ingredients shown in Tables 1 to 3, the adhesive agents are prepared (Examples 1 to 11).

On the other hand, the adhesive agents according to the ingredients shown in the following Table 4 were prepared to serve as Comparative Examples (Comparative Examples 1 to 5). Any adhesive agent was spread to contain 0.4 mg of diclofenac sodium per cm$^2$.

TABLE 1

| Ingredient | Example 1 | Example 2 | Example 3 | Example 4 |
|---|---|---|---|---|
| Diclofenac Na | 4 | 4 | 4 | 4 |
| Isostearic acid | 4 | 4 | 4 | 4 |

TABLE 1-continued

| Ingredient | Example 1 | Example 2 | Example 3 | Example 4 |
|---|---|---|---|---|
| Capric acid | | | | 4 |
| Oleic acid | 4 | | | |
| Linoleic acid | | 4 | | |
| Linolenic acid | | | 4 | |
| Crotamiton | 2 | 2 | 2 | 2 |
| Diethyl sebacate | 3 | 3 | 3 | 3 |
| Isopropryl myristate | 3 | 3 | 3 | 3 |
| SIS | 38 | 38 | 38 | 38 |
| Petroleum resin (P115) | 38 | 38 | 38 | 38 |
| Liquid gum (LIR-50) | 3 | 3 | 3 | 3 |
| Dibutylhydroxy toluene | 1 | 1 | 1 | 1 |

TABLE 2

| Ingredient | Example 5 | Example 6 | Example 7 | Example 8 |
|---|---|---|---|---|
| Diclofenac Na | 5 | 4 | 2 | 4 |
| Isostearic acid | 5 | 4 | 3 | 4 |
| Oleic acid | 5 | 4 | 3 | 4 |
| Crotamiton | 2 | 2 | 2 | 6 |
| Diethyl sebacate | 4 | 4 | 3 | 5 |
| Isopropryl myristate | 4 | 4 | 3 | 5 |
| SIS | 34 | 36 | 40 | 40 |
| Petroleum resin (P115) | 34 | 36 | 40 | 27 |
| Liquid gum (LIR-50) | 6 | 5 | 3 | 3 |
| Dibutylhydroxy toluene | 1 | 1 | 1 | 2 |

TABLE 3

| Ingredient | Example 9 | Example 10 | Example 11 |
|---|---|---|---|
| Diclofenac Na | 0.5 | 1 | 3 |
| Isostearic acid | 2 | 8 | 3 |
| Oleic acid | | 2 | 3 |
| Linoleic acid | 3 | | |
| Crotamiton | 1 | 2 | 2 |
| Diethyl sebacate | 1 | 3 | 3 |
| Isopropryl myristate | 0.5 | 3 | 3 |
| SIS | 36 | 47 | 45 |
| Petroleum resin (P115) | 50 | 30 | 36 |
| Liquid gum (LIR-50) | 5.8 | 3 | |
| Dibutylhydroxy toluene | 0.2 | 1 | 1 |
| 1-Menthol | | | 1 |

TABLE 4

| Ingredient | Comp. Example 1 | Comp. Example 2 | Comp. Example 3 | Comp. Example 4 | Comp. Example 5 |
|---|---|---|---|---|---|
| Diclofenac Na | 4 | 4 | 4 | 4 | 4 |
| Isostearic acid | | | | 4 | |
| Propionic acid | | | | 4 | |
| Capric acid | | | | | 8 |
| Oleic acid | 8 | | | | |
| Linoleic acid | | 8 | | | |
| Linolenic acid | | | 8 | | |
| Crotamiton | 2 | 2 | 2 | 2 | 2 |
| Diethyl sebacate | 3 | 3 | 3 | 3 | 3 |
| Isopropryl myristate | 3 | 3 | 3 | 3 | 3 |
| Petroleum resin (P115) | 38 | 38 | 38 | 38 | 38 |
| SIS | 38 | 38 | 38 | 38 | 38 |
| Liquid gum (LIR-50) | 3 | 3 | 3 | 3 | 3 |
| Dibutylhydroxy toluene | 1 | 1 | 1 | 1 | 1 |

Experiment 1. In Vitro Skin Permeability Test

[Test Method]

After removal of hairs of the abdomen of Wistar rats (male, 6 weeks old) with a shaver and a pair of clippers, the skin of the abdomen was taken out and was fixed in a Frantz diffusion cell. The test sample was fit on the skin. A physiological saline was used as a receptor solution. Water of about 37° C. was cyclized in a jacket over the cell. After that, sampling was carried out from time to time and the amount of diclofenac sodium permeated through the skin was measured by HPLC.

[Result]

The amounts of diclofenac sodium permeated through the skin after 24 hours on test samples were shown in the following Table.

TABLE 5

| Example | Amount of permeation (mcg/cell) | Comparative Example | Amount of permeation (mcg/cell) |
|---|---|---|---|
| 1 | 53.6 | 1 | 53.3 |
| 2 | 58.4 | 2 | 52.5 |
| 3 | 52.1 | 3 | 51.9 |
| 4 | 51.0 | 4 | 6.6 |
| | | 5 | 50.5 |

Experiment 2. Test of Skin Irritation

Test samples were spread on each back of volunteers (10 to 20 persons) for 24 hours. One hour later, 24 hours later and 48 hours later after tearing off the sample, judging was done by sight according to the following standard and the worst score was found.

Irritation index of the drug was calculated under the following formula.

| Standard of Judgement | Score |
|---|---|
| no reaction | 0 |
| slight erythema | 0.5 |
| erythema | 1.0 |
| erythema and edema | 2.0 |
| erythema, edema and papule, serous papule, small bulla | 3.0 |
| big bulla | 4.0 |

Irritation index=[total score of a volunteer]/[numbers of volunteers]×100

[Result]
Irritation indexes on each sample were shown in the following Table.

TABLE 6

| Example | Irritation index | Comparative Example | Irritation index |
|---|---|---|---|
| 1 | 6 | 1 | 140 |
| 2 | 13 | 2 | 180 |
| 3 | 0 | 3 | 100 |
| 4 | 8 | 5 | 90 |

As is clear from the above experimental results, the external oil patches containing diclofenac sodium of the present invention are far inferior to the preparations of Comparative Examples in skin irritation, although both preparations are almost same in the drug release.

Industrial Applicability

According to the present invention, there are prepared the preparations which show hardly irritation to skin without decrease of release of diclofenac sodium by combining a fatty acid having 10 to 18 carbon atoms which is liquid at room temperature together with isostearic acid in comparison with a case of using liquid fatty acid at room temperature solely.

What is claimed is:

1. An external oil patch consisting essentially of (i) diclofenac sodium, (ii) isostearic acid and (iii) a fatty acid having 10 to 18 carbon atoms, which is liquid at ordinary temperature, and which are combined in (iv) an adhesive, wherein the amount of diclofenac sodium is 0.5 to 6% by weight per total adhesive.

2. The external oil patch containing diclofenac sodium of claim 1 wherein the fatty acid is capric acid, oleic acid, linoleic acid or linolenic acid.

3. The external oil patch containing diclofenac sodium of claim 1 wherein the adhesive comprises 30–50% by weight of styrene-isoprene-styrene block copolymer, 25–50% by weight of a tackifier resin and 0.1–2% by weight of an antioxidant.

4. The external oil patch containing diclofenac sodium of claim 1 wherein the fatty acid is oleic acid or linolenic acid and the adhesive comprises 35–45% by weight of styrene-isoprene-styrene block copolymer, 35–40% by weight of a tackifier resin and 0.1–2% by weight of an antioxidant.

5. The external oil patch of claim 1, wherein the amount of fatty acid is 8 to 30% by weight per total adhesive.

6. The external oil patch of claim 1, wherein the fatty acid having 10 to 18 carbon atoms which are liquid at ordinary temperature is selected from the group consisting of capric acid, 2-undecylenic acid, 10-undecylenic acid, undecylic acid, trans-2-dodecenic acid, 2-hexyl decanoic acid, licinolic acid, linolenic acid, oleic acid, cis-6-octadecenoic acid, linoleic acid, and petroselinic acid.

7. The external oil patch of claim 1, wherein the ratio of isostearic acid to fatty acid having 10 to 18 carbon atoms and which is liquid at ordinary temperature is 8:2 to 4:6.

8. The external oil patch of claim 1, wherein the adhesive is selected from the group consisting of a rosin, terpene resin, petroleum resin, phenolic resin and xylene resin.

9. The external oil patch of claim 1, wherein the amount of the adhesive is 25 to 50% by weight of said external oil patch.

10. The external oil patch of claim 1, wherein the ratio of isostearic acid to fatty acid having 10 to 18 carbon atoms and which is liquid at ordinary temperature is 15:5 to 9:11.

11. The external oil patch of claim 1, wherein the ratio of isostearic acid to fatty acid having 10 to 18 carbon atoms and which is liquid at ordinary temperature is 7:3 to 5:5.

12. A method for applying diclofenac sodium to a patient in need thereof, which comprises applying the patch of claim 1 to the epidermis of said patient.

* * * * *